US008808692B2

(12) United States Patent
Kensil

(10) Patent No.: US 8,808,692 B2
(45) Date of Patent: Aug. 19, 2014

(54) COMPOSITIONS COMPRISING IMMUNOREACTIVE REAGENTS AND SAPONINS, AND METHODS OF USE THEREOF

(75) Inventor: Charlotte A. Kensil, Milford, MA (US)

(73) Assignee: CSL Limited, Parkville, Victoria (AU)

( * ) Notice: Subject to any disclaimer, the term of this patent is extended or adjusted under 35 U.S.C. 154(b) by 724 days.

(21) Appl. No.: 12/949,545

(22) Filed: Nov. 18, 2010

(65) Prior Publication Data

US 2011/0064749 A1  Mar. 17, 2011

Related U.S. Application Data

(62) Division of application No. 10/499,890, filed as application No. PCT/US02/40910 on Dec. 20, 2002, now abandoned.

(60) Provisional application No. 60/343,265, filed on Dec. 21, 2001.

(51) Int. Cl.
  *A61K 39/395* (2006.01)
  *A61K 45/06* (2006.01)
  *A61K 31/704* (2006.01)
  *A61K 39/00* (2006.01)

(52) U.S. Cl.
  CPC ............... *A61K 37/395* (2013.01); *A61K 45/06* (2013.01); *A61K 39/39558* (2013.01); *A61K 31/704* (2013.01); *A61K 2039/55577* (2013.01)
  USPC .................. 424/130.1; 424/138.1; 424/184.1

(58) Field of Classification Search
  None
  See application file for complete search history.

(56) References Cited

U.S. PATENT DOCUMENTS

| | | | |
|---|---|---|---|
| 5,057,540 A | 10/1991 | Kensil et al. | |
| 5,273,965 A | 12/1993 | Kensil et al. | |
| 5,443,829 A | 8/1995 | Kensil et al. | |
| 5,583,112 A | 12/1996 | Kensil et al. | |
| 5,612,030 A | 3/1997 | Chatterjee et al. | |
| 5,650,398 A | 7/1997 | Kensil et al. | |
| 5,716,848 A | 2/1998 | Dalsgard et al. | |
| 5,977,081 A | 11/1999 | Marciani | |
| 6,080,725 A | 6/2000 | Marciani | |
| 6,190,870 B1 | 2/2001 | Schmitz et al. | |
| 6,194,388 B1 | 2/2001 | Krieg et al. | |
| 6,207,646 B1 | 3/2001 | Krieg et al. | |
| 6,231,859 B1 | 5/2001 | Kensil | |
| 6,355,244 B1 | 3/2002 | Foon et al. | |
| 7,049,302 B1 | 5/2006 | Kensil | |
| 7,776,343 B1 | 8/2010 | Cox et al. | |
| 8,173,141 B2 | 5/2012 | Cox et al. | |
| 2003/0059937 A1 | 3/2003 | Ruben et al. | |
| 2003/0175884 A1 | 9/2003 | Umana et al. | |
| 2004/0191270 A1 | 9/2004 | Drane et al. | |
| 2006/0287263 A1 | 12/2006 | Davis et al. | |
| 2009/0017021 A1 | 1/2009 | Davis et al. | |

FOREIGN PATENT DOCUMENTS

| | | |
|---|---|---|
| JP | 7-242554 | 9/1995 |
| WO | WO 89/11296 A1 | 11/1989 |
| WO | WO 94/16731 A1 | 8/1994 |
| WO | WO 95/09179 | 4/1995 |
| WO | WO 98/40100 | 9/1998 |
| WO | WO 99/59578 A1 | 11/1999 |
| WO | WO 99/61056 | 12/1999 |
| WO | WO 00/03745 A2 | 1/2000 |
| WO | WO 00/62800 A2 | 10/2000 |
| WO | WO 00/72876 A2 | 12/2000 |
| WO | WO 01/15727 | 3/2001 |
| WO | WO 01/22972 | 4/2001 |
| WO | WO 01/51083 | 7/2001 |
| WO | WO 02/32450 A2 | 4/2012 |

OTHER PUBLICATIONS

U.S. Appl. No. 09/506,011, filed Feb. 17, 2000, Cox et al.
International Search Report issued on Mar. 25, 2003 in application No. PCT/US02/40910.
Office Action issued on Jul. 20, 2010 by the Examiner in U.S. Appl. No. 10/499,890 (US 2006/0210555).
Office Action issued on Dec. 16, 2009 by the Examiner U.S. Appl. No. 10/499,890 (US 2006/0210555).
Office Action issued on Apr. 22, 2009 by the Examiner U.S. Appl. No. 10/499,890 (US 2006/0210555).
Office Action issued on Dec. 31, 2008 by the Examiner in U.S. Appl. No. 10/499,890 (US 2006/0210555).
Office Action issued on May 12, 2008 by the Examiner in U.S. Appl. No. 10/499,890 (US 2006/0210555).
Office Action issued on Nov. 30, 2009 by the Examiner in U.S. Appl. No. 11/183,187 (US 2006/0287263).
Office Action issued on Oct. 5, 2009 by the Examiner in U.S. Appl. No. 11/183,187 (US 2006/0287263).

(Continued)

*Primary Examiner* — Yunsoo Kim

(74) *Attorney, Agent, or Firm* — Foley & Lardner LLP

(57) ABSTRACT

The present invention relates to pharmaceutical compositions that are useful for the prevention and treatment of infectious diseases, primary and metastatic neoplastic diseases (i.e., cancer), neurodegenerative or amyloid diseases, or any other disease wherein the treatment of such disease would be improved by an enhanced immune response, and methods of formulating the compositions. The compositions comprise an immunoreactive reagent (i.e., an antigen binding protein comprising an antigen binding region and a region or regions of an antibody that mediate antibody dependent immunological processes) and a saponin. The present invention also relates to methods of using the compositions of the invention for the prevention and/or treatment of infectious diseases, primary and metastatic neoplastic diseases (i.e., cancer), neurodegenerative or amyloid diseases, or any other disease wherein the treatment of such disease would be improved by an enhanced immune response.

17 Claims, No Drawings

(56) References Cited

OTHER PUBLICATIONS

Notice of Allowance issued on Oct. 26, 2009 by the Examiner in U.S. Appl. No. 09/506,011.
Berzofsky et al., "Progress on New Vaccine Strategies for immunotherapy and prevention of cancer," *Journal of Clinical Investigation*, vol. 113, No. 11, pp. 1515-1525, 2004.
Office Action issued on May 8, 2009, by the Examiner in U.S. Appl. No. 10/622,470 (US 2004/0191270).
Office Action issued on Sep. 2, 2008, by the Examiner in U.S. Appl. No. 10/622,470 (US 2004/0191270).
Office Action issued on Dec. 14, 2007, by the Examiner in U.S. Appl. No. 10/622,470 (US 2004/0191270).
Office Action issued on Jun. 6, 2007, by the Examiner in U.S. Appl. No. 10/622,470 (US 2004/0191270).
Office Action issued on Jan. 17, 2006, by the Examiner in U.S. Appl. No. 10/622,470 (US 2004/0191270).
Office Action issued on Mar. 24, 2005, by the Examiner in U.S. Appl. No. 10/622,470 (US 2004/0191270).
Office Action issued on Sep. 18, 2009, by the Examiner in U.S. Appl. No. 09/506,011.
Office Action issued on Jan. 27, 2009, by the Examiner in U.S. Appl. No. 09/506,011.
Office Action issued on Feb. 22, 2008, by the Examiner in U.S. Appl. No. 09/506,011.
Office Action issued on Oct. 18, 2006, by the Examiner in U.S. Appl. No. 09/506,011.
Office Action issued on Mar. 28, 2006, by the Examiner in U.S. Appl. No. 09/506,011.
Office Action issued on May 25, 2005, by the Examiner in U.S. Appl. No. 09/506,011.
Office Action issued on Nov. 17, 2003, by the Examiner in U.S. Appl. No. 09/506,011.
Office Action issued on Feb. 25, 2003, by the Examiner in U.S. Appl. No. 09/506,011.
Office Action issued on Feb. 13, 2002, by the Examiner in U.S. Appl. No. 09/506,011.
Office Action issued on May 23, 2001, by the Examiner in U.S. Appl. No. 09/506,011.
Office Action issued on Jun. 18, 2009, by the Examiner in U.S. Appl. No. 11/183,187 (US 2006/0287263).
Office Action issued on Sep. 16, 2008, by the Examiner in U.S. Appl. No. 11/183,187 (US 2006/0287263).
Office Action issued on Jul. 25, 2007, by the Examiner in U.S. Appl. No. 11/183,187 (US 2006/0287263).
Office Action issued on Mar. 7, 2007, by the Examiner in U.S. Appl. No. 11/183,187 (US 2006/0287263).
Office Action issued on Aug. 25, 2006, by the Examiner in U.S. Appl. No. 11/183,187 (US 2006/0287263).
Helling et al., "GM2-KLH conjugate vaccine: increased immunogenicity in melanoma patients after administration with immunological adjuvant QS-21," Cancer Res., 1995, pp. 2783-2788, vol. 55(13).
Higuchi et al., "Structure of desacylsaponins obtained from the bark of *Quillaja saponaria*," Phytochemistry, 1987, p. 229, vol. 26.
Kandimalla et al., "Effect of chemical modifications of cytosine and guanine in a CpG-motif of oligonucleotides: structure-immunostimulatory activity relationships," Bioorg. Med. Chem., 2001, pp. 807-813, vol. 9(3).
Keler et al., "Differential effect of cytokine treatment on Fc alpha receptor I- and Fc gamma receptor I mediated tumor cytotoxicity by monocyte-derived macrophages," J. Immunol., 2000, pp. 5746-5752, vol. 64(11).

Kensil et al., "Development of a genetically engineered vaccine against feline leukemia virus infection," J. Am. Vet. Med. Assoc., 1991, pp. 1423-1427, vol. 199(10).
Kensil et al., "Separation and characterization of saponins with adjuvant activity from *Quillaja saponaria* Molina cortex," J. Imrnunol. 1991, pp. 431-437, vol. 146(2).
Kensil et al., "Adjuvant activity of QS-21 isomers," Arm. N.Y. Acad Sci. 1993, pp. 392-395, vol. 690.
Kensil et al., "Structural and immunological characterization of the vaccine adjuvant QS-21," Vaccine Design: The Subunit and Adjuvant Approach, Powell and Newman eds., 1995, Plenum Press, New York.
Kersten et al., "Incorporation of the major outer membrane protein of *Neisseria gonorrhoeae* in saponin-lipid complexes (iscoms): chemical analysis, some structural features, and comparison of their immunogenicity with three other antigen delivery systems," Infect. Immun, 1988, pp. 432-438, vol. 56(2).
Lacaille-Dubois et al., "A review of the biological and pharmacological activities of saponins," Phytomedicine 1996, pp. 363-386, vol. 2.
Lewis et al., "Evaluation of CD8(+) T-cell frequencies by the Elispot assay in healthy individuals and in patients with metastatic melanoma immunized with tyrosinase peptide," Int. J. Cancer, 2000, pp. 391-398, vol. 87(3).
Livingston et al., "Phase I trial of immunological adjuvant QS-21 with a GM2 ganglioside-keyhole limpet haemocyanin conjugate vaccine in patients with malignant melano" Vaccine, 1994, pp. 1275-1280, vol. 12(14).
Livingston et al., "Impact of Immunological Adjuvants and Administration Route on HAA Response after Immunization with Marine Monoclonal Antibody MELIMMUNE-1 in Melanoma Patients," Vaccine Research, 1995, pp. 87-94, vol. 4(2).
Ma et al., "Impact of the saponin adjuvant QS-21 and aluminium hydroxide on the immunogenicity of recombinant OspA and OspB of *Borrelia burgdorferi*," Vaccine, 1994, p. 925, vol. 12(10).
Marciani et al., "Development of semisynthetic triterpenoid saponin derivatives with immune Ntimulating activity," Vaccine, 2000, pp. 3141-3151, vol. 18(27).
Newman et al., "Saponin adjuvant induction of ovalbumin-specific CD8+ cytotoxic T lymphocyte responses," J. Immunol., 1992, pp. 2357-2362, vol. 148(8).
Newman et al., "Induction of antigen-specific killer T lymphocyte responses using subunit SIVmac251 gag and env vaccines containing QS-21 saponin adjuvant," AIDS Res. Hum. Retroviruses, 1994, pp. 853-861, (7).
Soltysik et al., "Structure/function studies of QS-21 adjuvant: assessment of triterpene aldehyde and glucuronic acid roles in adjuvant function," *Vaccine*, 1995, pp. 1403-1410, vol. 13(15).
White et al., "A purified saponin acts as an adjuvant for a T-independent antigen," Immunobiology of Proteins and Peptides, 1991, pp. 207-210, vol. VI (Atassi ed.), Plenum Press, New York.
Woolridge et al., "Immunostimulatory Oligodeoxynucleotides Containing CpG Motifs Enhance the Efficacy of Monoclonal Antibody Therapy of Lymphoma," Blood, 1997, pp. 2994-2998, vol. 89.
Wu et al., "Saponin adjuvant enhancement of antigen-specific immune responses to an experimental HIV-1 vaccine," *J. Immunol.*, 1992, pp. 1519-1525, vol. 148(5).
Wu et al., "Accessory cell requirements for saponin adjuvant-induced class I MFIC antigen-restricted cytotoxic T-lymphocytes," Cell. Immunol., 1994, pp. 393-406, vol. 154(1).
Office Action issued on Feb. 15, 2011 by the Examiner in U.S. Appl. No. 10/499,890 (US 2006/0210555).
Pearse et al., "ISCOMATRIX® adjuvant for antigen delivery," Advanced Drug Delivery Reviews, vol. 57, pp. 465-474, 2005.

COMPOSITIONS COMPRISING IMMUNOREACTIVE REAGENTS AND SAPONINS, AND METHODS OF USE THEREOF

1. FIELD OF THE INVENTION

The present invention relates to pharmaceutical compositions that are useful for the prevention and treatment of infectious diseases, primary and metastatic neoplastic diseases (i.e., cancer), neurodegenerative or amyloid diseases, or any other disease wherein the treatment of such disease would be improved by an enhanced immune response, and methods of formulating the compositions. The compositions comprise an immunoreactive reagent (i.e., an antigen binding protein comprising an antigen binding region and a region or regions of an antibody that mediate antibody dependent immunological processes) and a saponin. Such antibody dependent processes include, but are not limited to, antibody dependent cellular cytotoxicity and phagocytosis. The present invention also relates to methods of using the compositions of the invention for the treatment of infectious diseases, primary and metastatic neoplastic diseases (i.e., cancer), neurodegenerative or amyloid diseases, or any other disease wherein the treatment of such disease would be improved by an enhanced immune response. Such methods include passive immunotherapy (i.e., passive immunization with an immunoreactive reagent, such as an antibody). Any such passive immunotherapy may be enhanced by the co-administration of a saponin, preferably QS-21.

2. BACKGROUND OF THE INVENTION

2.1. Passive Immunotherapy

Passive immunotherapy (also termed passive immunization) refers to the administration of an immunoreactive reagent (i.e., an antibody) comprising, for example, an antigen binding region directed against an epitope on a pathogen, tumor or pathogenic protein, and an Fc receptor-binding region, directly to a patient. The immunoreactive reagent can be given prophylactically to, for example, inhibit infection, or therapeutically to reduce or eliminate infection, to reduce or eliminate cancer cells, or to clear or remove pathogenic proteins, e.g., protein aggregates or deposits, as occurs in neurodegenerative and/or amyloidogenic disease. This is distinguished from immunization of a patient with a protein to induce an in vivo immune response to produce antibodies. Such administration preferably results in the stimulation of effector cells with Fc receptors capable of interacting with the Fc portion (i.e., the Fc receptor binding region) of the antibody or immunoreactive agent, resulting in cellular immune functions such as antibody-dependent cellular cytotoxicity (e.g., ADCC) or antibody-mediated opsonization and/or phagocytosis directed against the cell, pathogen, or protein possessing the epitope recognized by the immunoreactive agent. The saponin-mediated enhancement of passive immunotherapy can occur through stimulation of effector cells, i.e., induction and/or activiation of the Fc receptors on such cells. The efficacy of antibody-mediated tumor therapy which depends on FcR effector cell functions can be modified by the use of specific cytokines. Keler, et al., 2000, *J. Immunol.* 164:5746-5752.

2.2. Saponins

*Quillaja* saponins are a mixture of triterpene glycosides extracted from the bark of the tree *Quillaja saponaria*. They have long been recognized as immune stimulators that can be used as vaccine adjuvants, (Campbell and Peerbaye, 1992, *Res. Immunol.* 143(5):526-530), and a number of commercially available complex saponin extracts have been utilized as adjuvants. Crude saponins have been extensively employed as adjuvants in veterinary vaccines against foot and mouth disease, and in amplifying the protective immunity conferred by experimental vaccines against protozoal parasites such as malaria, *Trypanosoma cruzi* plasmodium, and the humoral response to sheep red blood cells (SRBC) (Bomford, 1982, *Int. Arch. Allerg. Appl. Immun.* 67:127).

The first commercially available *Quillaja* saponin adjuvants were crude extracts which, because of their variability, were not desirable for use in veterinary practice or in pharmaceutical compositions for man. An early attempt to purify *Quillaja* saponin adjuvants was made by Dalsgaard (1974, *Archiv fuer die gesamte Virusforschung* 44:243). Dalsgaard partially purified an aqueous extract of the saponin adjuvant material from *Quillaja saponaria* Molina. However, while Dalsgaard's preparation, "Quil-A," was a definite improvement over the previously available commercial saponins, it-still exhibited considerable heterogeneity.

Subsequent analysis via high-pressure liquid chromatography showed that Quil A was in fact a heterogeneous mixture of structurally related triterpene glycosides (U.S. Pat. No. 5,057,540; Kersten et al., 1988, *Infect. Immun.* 56:432-438; Kensil et al., 1991, *J. Immunol.* 146:431-437; Kensil et al., 1991, *J. Am. Vet. Med. Assoc.* 199:1423-1427). However, not all of these saponins were active as adjuvants.

The four most predominant purified *Quillaja* saponins are QS-7, QS-17, QS-18, and QS-21 (alternatively identified as QA-7, QA-17, QA-18, and QA-21). These saponins have been purified by HPLC and low pressure silica chromatography and were found to be adjuvant active, although differing in biological activities such as hemolysis and toxicity in mice. In particular, QS-21 and QS-7 were found to be least toxic in mice (Kensil et al., 1991, *J. Immunol.* 146:431-437).

Due to its potent adjuvant activity and low toxicity, QS-21 (commercially available as the "Stimulon®" adjuvant) has been identified as a useful immunological adjuvant (Kensil et al., 1995, "Structural and Immunological Characterization of the Vaccine Adjuvant QS-21," in Vaccine Design: The Subunit and Adjuvant Approach, Powell and Newman eds., Plenum Press, New York). QS-21 is a complex triterpene glycoside of quillaic acid. QS-21 is glycosylated at triterpene carbon 3, triterpene carbon 28, and carbon 5 of the second fatty acyl unit in a fatty acid domain.

More recently, QS-21 was further purified using hydrophilic interaction chromatography (HILIC) and resolved into two peaks, QS-21-V1 and QS-21-V2, which have been shown to be chemically different compounds. In C57BL/6 mice immunized with vaccines consisting of ovalbumin and either QS-21, QS-1-V1, or QS-21-V2, both of the individual components QS-21-V1 and QS-21-V2 are comparable in adjuvant effect to the original QS-21 peak (containing a mixture of 3:2 QS-21-V1 and QS-21-V2) for boosting the IgG subclasses IgG1, IgG2b, and IgG2 as well as the total IgG titer (U.S. Pat. No. 5,583,112, the entire contents of which are hereby incorporated by reference).

*Quillaja* saponins are structurally distinct from the saponins derived from other plant species. Two structural features that distinguish *Quillaja saponaria* saponins from those of other plant species are a fatty acid domain and a triterpene aldehyde at carbon 4 of the triterpene. (Kensil et al., 1995, "Structural and Immunological Characterization of the Vaccine Adjuvant QS-21," in Vaccine Design: The Subunit and Adjuvant Approach, Powell and Newman eds., Plenum Press, New York). Modifications to the aldehyde on the triterpene indicate that this functional group may be involved in the adjuvant mechanism (Soltysik et al., 1995, *Vaccine* 13(15):1403-1410).

*Quillaja* saponins, particularly QS-7,QS-17,QS-18,and QS-21,have been found to be excellent stimulators of antibody response to soluble T-dependent protein antigens, "subunit antigens," which are poorly immunogenic and require a potent adjuvant for maximization of immune responses. Examples of purified subunit antigens for which saponin adjuvants that augment the IgG response in mice include keyhole limpet hemocyanin (KLH), HIV-1 gp120 (Bomford et al., 1992, *AIDS Res. Hum. Retroviruses* 8:1765), and influenza nucleoprotein (Brett et al., 1993, *Immunology* 80:306). QS-7, QS-17,QS-18,and QS-21 have also been shown to stimulate potent antibody responses in mice to the antigens bovine serum albumin and cytochrome $b_5$ (Kensil et al., 1991, *J. Immunol.* 146:431). The level of antibody response induced by these purified saponins was comparable to other commonly used adjuvants, e.g., complete Freund's adjuvant, and superior to aluminum hydroxide.

QS-21 has also been shown to enhance antibody responses to T-independent antigens, including unconjugated bacterial polysaccharides (White et al., 1991, "A purified saponin acts as an adjuvant for a T-independent antigen," in: Immunobiology of Proteins and Peptides, Vol. VI (Atassi ed.), Plenum Press, New York, pp. 207-210). The immunogenicity of the vaccine was further increased by conjugating diphtheria toxoid to the polysaccharide. QS-21 enhanced the antibody response to the polysaccharide as well as the carrier, including IgG2a, IgG2b, and IgG3 responses (Coughlin et al., 1995, *Vaccine* 13(1):17-21).

The ability of adjuvants to modulate the isotype distribution and IgG subclass distribution of antibody response to an antigen through the promotion of Ig subclass switching has important implications for immunity to many bacterial and viral vaccines. QS-7,QS-17,QS-18,and QS-21 stimulate IgG2a response to cytochrome b5 after administration with saponin doses of 20 µg (Kensil et al., 1991, *J. Immunol* 146: 431). In this regard, QS-21 shifts predominant IgG1 responses to a profile that includes significant IgG2b and IgG2a responses. For example, QS-21 has been shown to stimulate antigen-specific IgG2a to a number of antigens, including *Borrelia burgdorferi* outer surface proteins OspA and OspB (Ma et al., 1994, *Vaccine* 12(10):925), feline leukemia virus (FeLV) envelope gp70 (Kensil et al., 1991, *J. Am. Vet. Med. Assoc.* 10:1423), human cytomegalovirus (HCMV) envelope protein gB (Britt et al., 1995, *J. Infect. Dis.* 171:18), respiratory synctial virus (RSV) purified fusion protein (Hancock et al., 1995, *Vaccine* 13(4):391), and tetanus toxoid (Coughlin et al., 1995, *Vaccine* 13(1):17). QS-21 has also been shown to induce boostable antibody responses (Britt et al., 1995, *J. Infect. Dis.* 171:18-25; Helling et al., 1995, *Cancer Res.* 55:2783-2788).

The ability of the QS-21 adjuvant to induce class I major histocompatibility complex (MHC) antigen-restricted cytotoxic T-lymphocyte responses (CTL) after immunization with soluble proteins is a characteristic of saponin adjuvants. A number of studies have shown the ability of QS-21 to induce potent cytotoxic T-lymphocyte (CTL) responses to various antigens, including ovalbumin (Wu et al., 1994, *Cell. Immunol.* 154:394-406; Newman et al., 1992, *J. Immunol.* 148(8):2357-2362), recombinant HIV-1 gp160 protein (Wu et al., 1992, *J. Immunol.* 148:1519), respiratory syncytial virus ("RSV") purified fusion protein (Hancock et al., 1995, *Vaccine* 13(4):391), and subunit $SIV_{mac251}$ gag and env (Newman et al., 1994, *AIDS Res. Hum. Retroviruses* 10(7): 853).

Most of the saponin adjuvant studies have been carried out in mice. However, the adjuvant activity of saponins is not limited to mice; it has also been demonstrated in humans, cats, dogs, guinea pigs, rabbits, pigs, sheep, cattle, and non-human primates. (Kensil et al., 1995, "Structural and Immunological Characterization of the Vaccine Adjuvant QS-21," in Vaccine Design: The Subunit and Adjuvant Approach, Powell, M. F. and Newman, M. J. eds., Plenuim Press, New York).

Phase 1 human trials of QS-21 with GM2 ganglioside-keyhole limpet haemocyanin conjugate vaccine have been conducted in patients with malignant melanoma (Livingston et al., 1994, *Vaccine* 12:1275-1280.Increased immunogenicity after administration with QS-21 adjuvant was observed (Helling et al., 1995, *Cancer Res.* 55:2783-2788). In another set of clinical trials, QS-21 was found to be a potent immunological adjuvant that significantly increased the serological response of melanoma patients to the murine anti-idiotype antibody MELIMMUNE-1 (Livingston et al., 1995, *Vaccine Res.* 4(2):87).

The immune adjuvant effect of saponins is dependent upon dose. Depending upon the antigen and the species, a minimum dose level of QS-21 is required for optimum response (Kensil et al., 1991, *J. Immunol.* 146(2):431-7; Kensil et al., 1993, *Ann N Y Acad Sci.* 690:392-5; Newman et al., 1992, *J. Immunol.* 148(5):1519-25; Livingston et al., 1994, *Vaccine* 12(14):1275-80). Below this minimum dose, the immune adjuvant effect is suboptimal (either low level or absent). QS-7 also has a dose response curve (Kensil et al., 1991, *J. Immunol.* 146(2):431-7).

Saponins have also been discovered to elicit an innate immune response which is independent of any particular antigen. The innate immunity stimulated by saponins results in a potentiated immune system that is capable of responding to an immunological challenge in an enhanced manner. For example, saponins are capable of increasing the production of TNF-alpha, IL-6 and MIP-1-alpha in macrophage cells. In bone marrow derived dendritic cells, saponins increase the production of MIP-1-alpha and IL-1,decrease the production of I1-12 and MIP-1-beta. This effect of saponins is described in International Patent Publication No. WO 01/51083,incorporated herein in its entirety. This property of saponins is different from their adjuvant effects in that an adjuvant effect is specific to the particular antigen with which the adjuvant is administered, while the innate immunity stimulation effect results in a general enhancement of the immune system and its ability to respond to a challenge which is independent of the particular antigen used to challenge. Measurements of innate immunity, and methods of determining enhancement thereof are known in the art, and are described in International Patent Publication No. WO 01/51083.

3. SUMMARY OF THE INVENTION

The present invention relates to pharmaceutical compositions that are useful for the prevention and treatment of infectious diseases, primary and metastatic neoplastic diseases (i.e., cancer), neurodegenerative or amyloid diseases, or any other disease wherein the treatment of such disease would be improved by an enhanced immune response, and methods of formulating the compositions. The compositions comprise an immunoreactive reagent (i.e., an antigen binding protein comprising an antigen binding region and a region that mediates one or more antibody dependent immunological processes) and a saponin. The compositions may further comprise an immunostimulatory oligonucleotide.

The present invention also relates to methods of using the compositions of the invention for the treatment of infectious diseases, primary and metastatic neoplastic diseases (i.e., cancer), neurodegenerative or amyloid diseases, or any other treatment of a disease that would be improved by an enhanced immune response. Such methods include passive immunotherapy. Any such passive immunotherapy may be enhanced by the co-administration of a saponin, preferably QS-21. The saponin may be administered concurrently with the immunoreactive reagent, or within a short time either before or after the administration of the immunoreactive reagent. A short time includes, but is not limited to 1, 15 or 30 minutes, 1, 6 or 12 hours, or 1 or 2 days. In a preferred embodiment, the saponin is QS-7, QS-17, QS-18, QS-21, QS-21-V1, or QS-21-V2.

The compositions of the invention can be used to generate an immune response against epitopes associated with neurodegenerative or amyloid diseases, cancer or an agent of infectious disease or any cell or molecule bearing an epitope associated with the aforementioned diseases, by administering to an individual a therapeutic amount of the immunoreactive reagent and saponin. Where an immune response against a type of cancer is desired, an immunoreactive reagent is used which specifically binds to (or "recognizes") an antigen of the type of cancer, i.e., a tumor-associated antigen. Where eliciting an immune response against an agent of an infectious disease is desired, an immunoreactive reagent is used which specifically binds to an antigen or pathologic protein (i.e., toxin) of the agent of infectious disease. In other embodiments, the compositions of the invention that comprise an immunoreactive reagent that specifically binds to an antigen of a type of cancer are used to treat or prevent the type of cancer; and the compositions of the invention that comprise an immunoreactive reagent that specifically binds to an agent of an infectious disease are used to treat or prevent the infectious disease. In other embodiments, the compositions of the invention comprise an immunoreactive reagent that specifically binds an antigenic molecule associated with a neurodegenerative disease or an amyloid disease ane are used to treat or prevent said neurodegenerative or amyloid disease.

Prophylactic and therapeutic dosage regimens and kits are also provided by the invention.

4. DETAILED DESCRIPTION OF THE INVENTION

The present invention relates to pharmaceutical compositions that are useful for the prevention and treatment of infectious diseases, primary and metastatic neoplastic diseases (i.e., cancer), neurodegenerative or amyloid diseases, or any other disease wherein the treatment of such disease would be improved by an enhanced immune response, and methods of formulating the compositions. In certain embodiments, the outcome of eliciting an immune response is prophylaxis or therapy. The compositions of the invention can be used to provide improved passive immunotherapy against cancer or an agent of infectious disease or neurodegenerative/amyloid diseases or any other disease or pathological state that can be treated by passive immunotherapy, by administering to an individual a therapeutic amount of the immunoreactive reagent and saponin.

Cancers that can be treated according to the methods of the invention include, but are not limited to, leukemia (e.g., acute leukemia such as acute lymphocytic leukemia and acute myelocytic leukemia), neoplasms, tumors (e.g., non-Hodgkin's lymphoma, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma), heavy chain disease (B-cell lymphoma), metastases, or any disease or disorder characterized by uncontrolled cell growth. Tumor antigens or tumor associated antigens include cancer-germ cell (CG) antigens (MAGE, NY-ESO-1), mutational antigens (MUM-1,p53,CDK-4), over-expressed self-antigens (p53, HER2/NEU), viral antigens (from Papilloma Virus, Epstein-Barr Virus), tumor proteins derived from non-primary open reading frame mRNA sequences (NY-ESO1, LAGE1), Melan A, MART-1,MAGE-1,MAGE-3,BAGE, GAGE-1,GAGE-2,tyrosinase, gp100, gp75,HER-2/neu, c-erb-B2,CEA, PSA, MUC-1,CA-125,Stn, TAG-72,KSA (17-1A), PSMA, p53 (point mutated and/or overexpressed), RAS (point mutated), EGF-R, VEGF, GD2,GM2,GD3,Anti-Id, CD20,CD19,CD22,CD36,Aberrant class II, B1, CD25 (IL-2R) (anti-TAC), or HPV.

Infectious agents that can be treated according to the invention include, but are not limited to viruses, such as hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral miningitis, encephalitis, dengue or small pox; bacteria, such as mycobacteria *rickettsia, mycoplasma, neisseria, S. pneumonia, Borrelia burgdorferi* (Lyme disease), *Bacillus antracis* (anthrax), tetanus, *streptococcus, staphylococcus, mycobacterium*,tetanus, pertissus, cholera, plague, diptheria, *chlamydia, S. aureus* and *legionella*; and agents of protozoal disease, such as *leishmania, kokzidioa, trypanosoma* or *malaria*.

Immunoreactive reagents specifically binding an antigenic molecule in or on a cell or structure, e.g., extracellular deposits or plaques comprising peptide and/or protein fibrils, that displays the hallmarks of a neurodegenerative or amyloid disease may also be utilized. Preferably, where it is desired to treat or prevent neurodegenerative or amyloid diseases, immunoreactive reagents that specifically bind to molecules comprising epitopes of antigenic molecules associated with neurodegenerative diseases, or epitopes of antigenic molecules associated with amyloid diseases, including but not limited to fibril peptides or proteins, are used. Such neurodegenerative disease-associated antigenic molecules may be molecules associated with Alzheimer's Disease, age-related loss of cognitive function, senile dementia, Parkinson's disease, amyotrophic lateral sclerosis, Wilson's Disease, cerebral palsy, progressive supranuclear palsy, Guam disease, Lewy body dementia, prion diseases, spongiform encephalopathies, Creutzfeldt-Jakob disease, polyglutamine diseases, Huntington's disease, myotonic dystrophy, Freidrich's ataxia, ataxia, Gilles de la Tourette's syndrome, seizure disorders, epilepsy, chronic seizure disorder, stroke, brain trauma, spinal cord trauma, AIDS dementia, alcoholism, autism, retinal ischemia, glaucoma, autonomic function disorder, hypertension, neuropsychiatric disorder, schizophrenia, or schizoaffective disorder. Examples of such antigentic molecules are disclosed in U.S. application Ser. No. 09/489,216,which is incorporated by reference herein in its entirety, and include, but are not limited to, β-amyloid or a fragment thereof, an oligomeric Aβ complex or a fragment thereof, an ApoE4-Aβ complex, tau protein or a fragment thereof, amyloid precursor protein or a fragment thereof, a mutant amyloid precursor protein or a fragment thereof, presenillin or a fragment thereof, a mutant of presenillin or a fragment thereof, α-synuclein or a fragment thereof, or a prion protein or a fragment thereof, and the antigenic derivatives of any of the foregoing proteins or fragments thereof. Amyloid disease associated antigenic molecules may be molecules associated with diseases characterized by the extracellular deposition of protein and/or peptide fibrils which form amyloid deposits or plaques, including but not limited to type II diabetes and amyloidoses associated with chronic inflammatory or infectious disease states and malignant neoplasms, e.g., myeloma. Certain amyloid disease such as Alzheimer's disease and prion diseases, e.g., Creutzfeldt Jacob disease, are neurodegenerative diseases.

The treatment of other disease or pathogenic states that can be treated by immunotherapy may are also within the scope of the present invention. Such treatment includes the treatment of cardiovascular disease with an immunoreactive reagent that binds angiotensin 2,and the treatment of autoimmune associated diseases, such as arthritis, with immunoreactive reagents that bind IL-10,tumor necrosis factor, or other immunoregulatory molecules.

The compositions comprise an immunoreactive reagent (i.e., an antigen binding protein comprising an antigen binding region and a region that mediates one or more antibody dependent immunological processes, e.g., an Fc receptor-binding region) and a saponin. In certain embodiments, the compositions of the invention further include an immunostimulatory oligonucleotide.

The present invention also relates to methods of using the compositions of the invention for the treatment of infectious diseases, primary and metastatic neoplastic diseases (i.e., cancer), neurodegenerative or amyloid diseases, or any other treatment of a disease that would be improved by an enhanced immune response. Such methods include passive immunotherapy. Any such passive immunotherapy may be enhanced by the co-administration of a saponin, preferably QS-21.The saponin may be administered concurrently with the immunoreactive reagent, or within a short time either before or after he administration of the immunoreactive reagent. A short time includes, but is not limited to 1, 15 or 30 minutes, 1, 6, 12, 18 or 36 hours, or 1 or 2 days.

In a preferred embodiment, the saponin is QS-7,QS-21, QS-21-V1,or QS-21-V2.In another embodiment, the saponin is an active derivative, e.g., semi-synthetic derivatives such as GPI-100,as well as other immuostimulatory (e.g., adjuvant active) saponins or saponin-containing compositions. The adjuvant, haemolytic, and innate immune stimulatory activities of individual saponins have been extensively studied in the art. (Lacaille-Dubois and Wagner, 1996 "A review of the biological and pharmacological activities of saponins." *Phytomedicine* vol. 2,pp 363-386,incorporated herein by reference in its entirety). Such active saponins include Quil A and fractions thereof, ISCOMS, saponins derived from other plant species such as Gypsophila and Saponaria (Bomford et al., 1992, *Vaccine* 10(9):572-577,incorporated herein by reference in its entirety), and *Chenopodium quina* saponins have been used in both intranasai and intragastric vaccines (Estrada et al., 1998, *Comp. Immunol. Microbiol. Infect. Dis.* 21(3):225-36,incorporated herein by reference in its entirety).

The compositions can be utilized for the prevention of a variety of cancers, e.g., in individuals who are predisposed as a result of familial history or in individuals with an enhanced risk to cancer due to environmental factors, for the prevention of infectious diseases, e.g., in individuals with enhanced risks of exposure to agents of infectious disease, and for the prevention of neurodegenerative or amyloid diseases, for example in individuals with genetic predispositions to neurodegenerative or amyloid diseases.

The invention also provides kits comprising one or more containers with one or more of the ingredients of the pharmaceutical compositions of the invention. Optionally associated with such kit(s) can be a notice in the form prescribed by a governmental agency regulating the manufacture, use or sale of pharmaceuticals or biological products, which notice reflects approval by the agency of manufacture, use or sale for human administration. In one embodiment, the kits can optionally further comprise a predetermined amount of the immunoreative reagent (i.e., an antigen binding protein comprising an antigen binding region and a region that mediates one or more antibody dependent immunological processes, e.g., an Fc receptor-binding region) and a saponin. In a preferred embodiment, the kit comprises the immunoreactive reagent and the saponin in separate containers.

4.1. Immunoreactive Reagents

The immunoreactive reagents of the invention are peptides comprising 1) an antigen binding region and, optionally, 2) a region that mediates one or more antibody dependent immunological processes. The antigen binding region can comprise or consist of the antigen binding region of an antibody. The antigen binding region can comprise any peptide or domain that interacts specifically with an antigen of interest. For example, the antigen binding region can be a ligand or other specific binding partner of the antigen of interest, or can be a fragment of such ligand or binding partner, or can be derived from such ligand or binding partner.

The region that mediates one or more antibody dependent immunological processes can comprise or consist of a region that is capable of binding an Fc receptor, e.g., the portion of an antibody that binds Fc receptors, or a region that binds complement, e.g., the complement binding region of an antibody. This region can also be an antigen binding domain of an antibody that binds to Fc receptors or complement.

Immunoreactive reagents include antibodies, Fab and F(ab')$_2$ fragments, molecules or proteins engineered to include the antigen binding portion of an antibody, molecules or proteins engineered to include an antigen binding domain that mediates antibody dependent immune responses, a peptide or domain that interacts specifically with the antigen of interest, or any antigen binding domain that interacts with an antigen/epitope of interest, and the domain of the constant region of an antibody that mediates antibody dependent immune effector cell responses or processes. Examples of such domains or regions within the Ab constant region that can be used in the present invention include those disclosed in Reddy et al., 2000, *J. Immunol.* 164(4):1925-33; Coloma et al., 1997, *Nat Biotechnol.* 15(2):159-63; Carayannopoulos et al., 1994, *Proc Natl. Acad. Sci. U.S.A.* 91(18):8348-52; Morrison, 1992, *Annu Recombinant expression vector Immunol.*

10:239-65; Traunecker et al., 1992, *Int. J. Cancer Suppl.*, 7:51-2; Gillies et al., 1990, *Hum. Antibodies Hybridomas*, 1(1):47-54; each of which is incorporated herein by reference in its entirety.

Such antibody dependent processes include, but are not limited to, antibody dependent cellular cytotoxicity, activation of complement, opsonization and phagocytosis. The effector cells that mediate certain antibody dependent processes include monocytes, macrophages, natural killer cells, and polymorphonuclear cells. Without being bound by a particular mechanism, it is thought that saponins are able to increase receptors on the effector cells responsible for mediating the antibody dependent response. These receptors include the Fc alpha and Fc gamma receptors, isoforms thereof, or any combination thereof. Thus, in a particular embodiment, the region of the immunoreactive reagent that mediates one or more antibody dependent immunological processes comprises or consists of a region that is a ligand for Fc receptors, preferably the Fc α receptor or the Fc gamma receptor, or both. In another embodiment, the region of the immunoreactive reagent that mediates one or more antibody dependent immunological processes comprises or consists of a region that stimulates the function of immune effector cells, preferably monocytes, macrophages, natural killer cells, polymorphonuclear cells, or any combination of two or more of such cells, such that a prophylactic and/or therapeutic effect is achieved.

In a preferred embodiment, the immunoreactive reagent is an antibody, or a composition comprising an antibody such as serum. In a particular embodiment, the immunoreactive reagent is an IgA, IgG or IgM antibody, or comprises a fragment thereof. In a particularly preferred embodiment, the immunoreactive reagent is a monoclonal antibody, or includes fragments of a monoclonal antibody. The immunoreactive reagent may also comprise or consist of human immune globulin for treatment of Hepatitis B; Respigam for the treatment of RSV; Sandoglobulin, or ImmuneGlobulin IV (IGIV). In another embodiment, the immunoreactive reagent is not directed towards any single epitope, but instead comprises a mixture of one or more molecules that bind to a population of epitopes. An example of such an immunoreactive reagent is serum or antibodies concentrated from serum or plasma. Such serum or plasma may be from a subject immunized against a particular antigen, or from a subject not so immunized.

In another embodiment, the immunoreactive reagent is a bi-specific molecule having two antigen binding regions of different specificity, i.e., one recognizing an epitope on a target cell or protein, and the other recognizing an epitope of an effector cell, e.g., an epitope of FcR. In another embodiment, the immunoreactive reagent is a bi-specific molecule having two antigen binding domains for different epitopes on the target cell/protein; and a domain that mediates antibody dependent immune responses. Such bi-specific molecules that target cancer cells or pathogens and their therapeutic effects have been examined both in vivo and in vitro (e.g., Wallace et al., 2001, *J Immunol. Methods* 248(1-2):167-82; Sundarapandiyan et al., 2001, *J. Immunol. Methods* 248(1-2):113-23; Honeychurch et al., 2000, *Blood* 96(10):3544-52; Negri et al., 1995, *Br J Cancer* 72(4):928-33; Wang et al., 1994, *Zhonghua Zhong Liu Za Zhi* 16(2):83-7,Chinese) (each of which is incorporated by reference in its entirety).

In a preferred embodiment, the immunoreactive reagent is purified. "Purified" as used herein to describe certain peptides, antibodies, molecules, proteins, antigens, saponins, and the like, refer to a state beyond that in which the molecules, proteins, antigens, and the like, are separated from greater than 1%, 5%, 10%, 20%, 30%, 40%, 50%, 60%, 70%, 80%, 90%, 95%, or 99% of the proteins, polysaccharides, and/or lipids with which the peptides, antibodies, molecules, proteins, antigens, saponins, and the like are normally associated naturally. If the isolated molecules, proteins, antigens, saponins, and the like are synthesized, they are contaminated with less than 50%, 40%, 30%, 20%, 10%, 5%, 1% or 0.1% of the chemical precursors or synthesis reagents used to synthesize the molecules, proteins, antigens, saponins, and the like. In preferred embodiments the peptides, antibodies, molecules, proteins, antigens, saponins, and the like are at least 1% pure, 5% pure, 10% pure, 20% pure, 30% pure, 40% pure, 50% pure, 60% pure, 70% pure, 80% pure, 90% pure, 95% pure, 99% pure, or 100% pure. As used herein, the term "% pure" indicates the percentage of the total composition that is made up of the molecule of interest, by weight. Thus, a composition of 100 grams containing 50 grams of a molecule of interest is 50% pure with respect to the molecule of interest.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas, pp. 563-681 (Elsevier, N.Y., 1981) (both of which are incorporated herein by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In a non-limiting example, mice can be immunized with an antigen of interest or a cell expressing such an antigen. Once an immune response is detected, e.g., antibodies specific for the antigen are detected in the mouse serum, the mouse spleen is harvested and splenocytes isolated. The splenocytes are then fused by well known techniques to any suitable myeloma cells. Hybridomas are selected and cloned by limiting dilution. The hybridoma clones are then assayed by methods known in the art for cells that secrete antibodies capable of binding the antigen. Ascites fluid, which generally contains high levels of antibodies, can be generated by inoculating mice intraperitoneally with positive hybridoma clones.

Antibody fragments which recognize specific epitopes may be generated by known techniques. For example, Fab and F(ab')$_2$ fragments may be produced by proteolytic cleavage of immunoglobulin molecules, using enzymes such as papain (to produce Fab fragments) or pepsin (to produce F(ab')$_2$ fragments). F(ab')$_2$ fragments contain the complete light chain, and the variable region, the CH1 region and the hinge region of the heavy chain.

For example, antibodies can also be generated using various phage display methods known in the art. In phage display methods, functional antibody domains are displayed on the surface of phage particles which carry the polynucleotide sequences encoding them. In a particular embodiment, such phage can be utilized to display antigen binding domains, such as Fab and Fv or disulfide-bond stabilized Fv, expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage, including fd and M13. The antigen binding domains are expressed as a recombinantly fused protein to either the phage gene III or gene VIII protein. Examples of phage display methods that can be used to make the immunoglobulins, or fragments thereof, of the present invention include those disclosed in Brinkman et al., 1995, *J. Immunol. Methods* 182:41-50; Ames et al., 1995, *J. Immunol. Methods* 184:177-186; Kettleborough et al., 1994, *Eur. J. Immunol.*, 24:952-958; Persic et al., 1997, *Gene* 187:9-18; Burton et al., 1994, *Advances in Immunology* 57:191-280; PCT application No. PCT/GB91/01134; PCT publications WO 90/02809; WO 91/10737; WO 92/01047; WO 92/18619; WO 93/1 1236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., 1992, *BioTechniques* 12(6): 864-869; and Sawai et al., 1995, *AJRI* 34:26-34; and Better et al., 1988, *Science* 240:1041-1043 (each of which is incorporated by reference in its entirety). Examples of techniques which can be used to produce single-chain Fvs and antibodies include those described in U.S. Pat. Nos. 4,946,778 and 5,258,498; Huston et al., 1991, *Methods in Enzymology* 203: 46-88; Shu et al., 1993, *PNAS* 90:7995-7999; and Skerra et al., 1988, *Science* 240:1038-1040.

For some uses, including in vivo use of antibodies in humans, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Reichmann et al., 1988, *Nature* 332:323, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530,101 and 5,585,089), veneering or resurfacing (EP 592,106; EP 519,596; Padlan, 1991, *Molecular Immunology* 28(4/5):489-498; Studnicka et al., 1994, *Protein Engineering* 7(6):805-814; Roguska et al., 1994, *Proc Natl. Acad. Sci. USA*, 91:969-973), and chain shuffling (U.S. Pat. No. 5,565,332), all of which are hereby incorporated by reference in their entireties.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Freemont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., 1988, *Bio/technology* 12:899-903).

In a preferred embodiment, the antibodies have in vivo therapeutic and/or prophylactic uses. Examples of therapeutic and prophylactic antibodies include, but are not limited to, SYNAGIS® (MedImmune, Md.) which is a humanized anti-respiratory syncytial virus (RSV) monoclonal antibody for the treatment of patients with RSV infection; HERCEPTIN® (Trastuzumab) (Genentech, Calif.) which is a humanized anti-HER2 monoclonal antibody for the treatment of patients with metastatic breast cancer; REMICADE® (infliximab) (Centocor, Pa.) which is a chimeric anti-TNFα monoclonal antibody for the treatment of patients with Crone's disease; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); Ostavir which is a human anti Hepatitis B virus antibody (Protein Design Lab/Novartis); PROTOVIR™ which is a humanized anti-CMV IgG1 antibody (Protein Design Lab/Novartis); MAK-195 (SEGARD) which is a murine anti-TNF-α F(ab')$_2$ (Knoll Pharma/BASF);

IC14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-1A cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DIAGNOSTIC REAGENT antibody (Techniclone); ABX-IL8 is a human anti-IL8 antibody (Abgenix); anti-CD11a is a humanized IgG1 antibody (Genentech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (DEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); SCH55700 is a humanized anti-IL-5 IgG4 antibody (Celltech/Schering); SB-240563 and SB-240683 are humanized anti-IL-5 and IL-4 antibodies, respectively, (SmithKline Beecham); rhuMab-E25 is a humanized anti-IgE IgG1 antibody (Genentech/Norvartis/Tanox Biosystems); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor). The above-listed immunoreactive reagents, as well as any other immunoreactive reagents, may be administered according to any regimen known to those of skill in the art, including the regimens recommended by the suppliers of the immunoreactive reagents. Immunoreactive reagents that bind to 4-1BB glycoprotein or Cytotoxic T Lymphocyte Antigen-4 (CTLA-4), such as antibodies specific for 4-1BB or CTLA-4,respectively, are also contemplated within the present invention.

The immunoreactive reagents of the invention can be produced by any method known in the art for the synthesis of antibodies, in particular, by chemical synthesis or preferably, by recombinant expression techniques. Such methods are described below with reference to an antibody immunoreactive reagent, but are readily applicable to the production of other immunoreactive reagents.

The nucleotide sequence encoding an antibody or other immunoreactive reagent may be obtained from any information available to those of skill in the art (i.e., from Genbank, the literature, or by routine cloning). If a clone containing a nucleic acid encoding a particular antibody or an epitope-binding fragment thereof or other immunoreactive reagent is not available, but the sequence of the antibody molecule or epitope-binding fragment thereof or other immunoreactive reagent is known, a nucleic acid encoding the immunoglobulin or other immunoreactive reagent may be chemically synthesized or obtained from a suitable source (e.g., an antibody cDNA library, or a cDNA library generated from, or nucleic acid, preferably poly A$^+$ RNA, isolated from any tissue or cells expressing the antibody, such as hybridoma cells selected to express an antibody) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art. In the case of immunoreactive reagents that do not exist in nature, nucleic acids encoding the different regions of the immunoreactive reagent can be obtained from preexisting libraries or known genes, or can be synthesized.

Once the nucleotide sequence of the antibody or other immunoreactive reagent is determined, the nucleotide sequence of the antibody or other immunoreactive reagent may be manipulated using methods well known in the art for the manipulation of nucleotide sequences, e.g., recombinant DNA techniques, site directed mutagenesis, PCR, etc. (see, for example, the techniques described in Sambrook et al., 1990, *Molecular Cloning, A Laboratory Manual*, 2d Ed., Cold Spring Harbor Laboratory, Cold Spring Harbor, N.Y.; and Ausubel et al., eds., 1998, *Current Protocols in Molecular Biology*, John Wiley & Sons, NY, which are both incorporated by reference herein in their entireties), to generate antibodies or other immunoreactive reagent having a different amino acid sequence by, for example, introducing amino acid substitutions, deletions, and/or insertions into the epitope-binding domain regions of the antibodies or other immunoreactive reagent or into the constant (Fc) regions of the antibodies or other immunoreactive reagent which are involved in the interaction with immune effector cells.

Recombinant expression of an antibody or other immunoreactive reagent requires construction of an expression vector containing a nucleotide sequence that encodes the antibody or other immunoreactive reagent. Once a nucleotide sequence encoding an antibody molecule or a heavy or light chain of an antibody, or portion thereof (preferably, but not necessarily, containing the heavy or light chain variable region) or other immunoreactive reagent has been obtained, the vector for the production of the antibody molecule or other immunoreactive reagent may be produced by recombinant DNA technology using techniques well known in the art. Thus, methods for preparing a protein by expressing a polynucleotide containing an antibody or other immunoreactive reagent encoding nucleotide sequence are described herein. Methods which are well known to those skilled in the art can be used to construct expression vectors containing antibody or other immunoreactive reagent coding sequences and appropriate transcriptional and translational control signals.

These methods include, for example, in vitro recombinant DNA techniques, synthetic techniques, and in vivo genetic recombination. The nucleotide sequence encoding the heavy-chain variable or constant region, light-chain variable or constant region, both the heavy-chain and light-chain variable regions, an epitope-binding fragment of the heavy- and/or light-chain variable region, or one or more complementarity determining regions (CDRs) of an antibody or other immunoreactive reagent may be cloned into such a vector for expression. The expression vector is transferred to a host cell by conventional techniques and the transfected cells are then cultured by conventional techniques.

A variety of host-expression vector systems may be utilized to express the antibody molecules or other immunoreactive reagent of the invention. Such host-expression systems represent vehicles by which the coding sequences of interest may be produced and subsequently purified, but also represent cells which may, when transformed or transfected with the appropriate nucleotide coding sequences, express an antibody molecule or other immunoreactive reagent of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing antibody or other immunoreactive reagent coding sequences; yeast (e.g., *Saccharomyces* and *Pichia*) transformed with recombinant yeast expression vectors containing antibody or other immunoreactive reagent coding sequences; insect cell systems infected with recombinant virus expression vectors (e.g., baculovirus) containing antibody or other immunoreactive reagent coding sequences; plant cell systems infected with recombinant virus expression vectors (e.g., cauliflower mosaic virus, CaMV; and tobacco mosaic virus, TMV) or transformed with recombinant plasmid expression vectors (e.g., Ti plasmid) containing antibody or other immunoreactive reagent coding sequences; and mammalian cell systems (e.g., COS, CHO, BHK, 293, 3T3 and NSO cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule or other immunoreactive reagent, are used for the expression of a recombinant antibody or other immunoreactive reagent molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, *Gene* 45:101,and Cockett et al., 1990, *Bio/Technology* 8:2).

In bacterial systems, a number of expression vectors may be advantageously selected depending upon the use intended for the antibody molecule or other immunoreactive reagent being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, *EMBO* 12:1791), in which the antibody or other immunoreactive reagent coding sequence may be ligated individually into the vector in frame with the lacZ coding region so that a fusion protein is produced; and pIN vectors (Inouye & Inouye, 1985, *Nucleic Acids Res.* 13:3101-3109,and Van Heeke & Schuster, 1989, *J. Biol. Chem.* 24:5503-5509).

In an insect system, *Autographa californica* nuclear polyhedrosis virus (AcNPV) is used as a vector to express foreign genes. The virus grows in *Spodoptera frugiperda* cells. The antibody or other immunoreactive reagent coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized to express an antibody molecule or other immunoreactive reagent of the invention. In cases where an adenovirus is used as an expression vector, the antibody or other immunoreactive reagent coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule or other immunoreactive reagent in infected hosts (e.g., see Logan & Shenk, 1984, *Proc. Natl. Acad. Sci. USA* 81:355-359). Specific initiation signals may also be required for efficient translation of inserted antibody or other immunoreactive reagent coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bitter et al., 1987, *Methods in Enzymol.* 153:516-544).

In addition, a host cell strain may be chosen which modulates the expression of the antibody or other immunoreactive reagent sequences, or modifies and processes the antibody or other immunoreactive reagent in the specific fashion desired. Such modifications (e.g., glycosylation) and processing (e.g., cleavage) of protein products may be important for the function of the antibody or other immunoreactive reagent. Different host cells have characteristic and specific mechanisms for the post-translational processing and modification of proteins and gene products. Appropriate cell lines or host systems can be chosen to ensure the correct modification and processing of the antibody or other immunoreactive reagent expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138,and in particular, myeloma cells such as NSO cells, and related cell lines, see, for example, Morrison et al., U.S. Pat. No. 5,807,715,which is hereby incorporated by reference in its entirety.

For long-term, high-yield production of recombinant antibodies or other immunoreactive reagent, stable expression is preferred. For example, cell lines which stably express the antibody molecule or other immunoreactive reagents may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule or other immunoreactive reagent. Such engineered cell lines may be particularly useful in screening and evaluation of compositions that interact directly or indirectly with the antibody molecule or other immunoreactive reagent.

A number of selection systems may be used, including but not limited to, the herpes simplex virus thymidine kinase (Wigler et al., 1977, *Cell* 11:223), hypoxanthine-guanine phosphoribosyltransferase (Szybalska & Szybalski, 1992, *Proc. Natl. Acad. Sci. USA* 48:202), and adenine phosphoribosyltransferase (Lowy et al., 1980, *Cell* 22:8-17) genes can be employed in tk$^-$, hgprt$^-$ or aprt$^-$ cells, respectively. Also, antimetabolite resistance can be used as the basis of selection for the following genes: dhfr, which confers resistance to methotrexate (Wigler et al., 1980, *Natl. Acad. Sci. USA* 77:357,and O'Hare et al., 1981, *Proc. Natl. Acad. Sci. USA* 78:1527); gpt, which confers resistance to mycophenolic acid (Mulligan & Berg, 1981, *Proc. Natl. Acad. Sci. USA* 78:2072); neo, which confers resistance to the aminoglycoside G-418 (Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62: 191-217; and May, 1993, *TIB TECH* 11(5):155-2 15); and hygro, which confers resistance to hygromycin (Santerre et al., 1984, *Gene* 30:147). Methods commonly known in the art of recombinant DNA technology may be routinely applied to select the desired recombinant clone, and such methods are described, for example, in Ausubel et al. (eds.), 1993, *Current Protocols in Molecular Biology*,John Wiley & Sons, NY; Kriegler, 1990, *Gene Transfer and Expression, A Laboratory Manual*, Stockton Press, NY; in Chapters 12 and 13,Dracopoli et al. (eds), 1994, *Current Protocols in Human Genetics*, John Wiley & Sons, NY; and Colberre-Garapin et al., 1981, *J. Mol. Biol.* 150:1,which are incorporated by reference herein in their entireties.

The expression levels of an antibody molecule or other immunoreactive reagent can be increased by vector amplification (for a review, see Bebbington and Hentschel, 1987, *The use of vectors based on gene amplification for the expression of cloned genes in mammalian cells in DNA 'cloning*,Vol. 3.Academic Press, New York). When a marker in the vector system expressing antibody or other immunoreactive reagent is amplifiable, increase in the level of inhibitor present in culture of host cell will increase the number of copies of the marker gene. Since the amplified region is associated with the antibody or other immunoreactive reagent gene, production of the antibody or other immunoreactive reagent will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides or different selectable markers to ensure maintenance of both plasmids. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, *Nature* 322:52; and Kohler, 1980, *Proc. Natl. Acad. Sci. USA* 77:2 197). The coding sequences for the heavy and light chains may comprise cDNA or genomic DNA.

Once an antibody or other immunoreactive reagent molecule of the invention has been produced by recombinant expression, it may be purified by any method known in the art for purification of an immunoglobulin molecule or other immunoreactive reagent, for example, by chromatography (e.g., ion exchange, affinity, particularly by affinity for the specific antigen after Protein A purification, and sizing column chromatography), centrifugation, differential solubility, or by any other standard techniques for the purification of proteins. Further, the antibodies or other immunoreactive reagents of the present invention or fragments thereof may be fused to heterologous polypeptide sequences described herein or otherwise known in the art to facilitate purification.

4.2. Sources of Saponins

Any saponin or saponin preparation known in the art may be used in the compositions and methods of the invention. The term "saponin" as used herein includes glycosidic triterpenoid compounds which produce foam in aqueous solution and have hemolytic activity in most cases. The invention encompasses the use of saponins per se, as well as natural and pharmaceutically acceptable salts and pharmaceutically acceptable derivatives thereof. The term "saponin" also embodies biologically active fragments thereof. The term "saponin" also encompasses chemically modified saponins, such as GPI-0100,and other modified saponins described, for example, in U.S. Pat. Nos. 6,080,725; 5,977,081,and 5,443,829,each of which is incorporated herein in its entirety. The use of modified saponins adapted for, e.g., drug delivery, such as those described in U.S. Pat. Nos. 5,650,398; 5,443,829 and 5,273,965,each of which is incorporated herein in its entirety, is also encompassed by the invention. Preferably, the saponin is a single saponin. In other embodiments of the invention, the term "saponin" covers mixtures of saponins. Suitable saponins include QS-7,QS-17,QS-18 and QS-21. Preferably, the mixture of saponins comprises two or more substantially pure saponins. More preferably, the two or more substantially pure saponins are from *Quillaja saponaria* in doses that are otherwise suboptimal for the individual saponins. In a particularly preferred embodiment, the combination of saponins consists essentially of two substantially pure saponins QS-7 and QS-21 or, in other particularly preferred embodiments, QS-7 and QS-21-V1 or QS-7 and QS-21-V2,as described in U.S. Pat. No. 6,231,859,which is herein incorporated by reference in its entirety. As used herein, "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds. A number of non-limiting examples of saponins and their methods of preparation are provided below.

Saponins suitable for use in an individual are soluble in aqueous solution and can be reconstituted from lyophilized or dried saponins. Specific saponins useful for the present invention include, but are not limited to, the "Quil-A" adjuvant preparation sold by Superfos of Denmark, and the chromatographic fractions with adjuvant activity that are described in U.S. Pat. Nos. 5,057,540 and 5,583,112,particularly fractions QS-21 (also referred to in the patents as QA-21) and QS-7.

Also useful in the methods and compositions of the present invention are chemically modified saponins that retain immune stimulating activity. According to Kensil et al., U.S. Pat. No. 5,583,112,the contents of which are fully incorporated by reference herein, the carboxyl group on the glucuronic acid of saponins from *Quillaja saponaria* Molina can be conjugated to a protein, a peptide, or a small molecule containing a primary amine. According to Higuchi et al., 1987, *Phytochemistry* 26:229,saponins from *Quillaja saponaria* may be deacylated by alkaline-catalyzed hydrolysis. According to Marciani et al., U.S. Pat. No. 5,977,081,the contents of which are fully incorporated by reference herein, the carboxyl group on the glucuronic acid of nonacylated or deacylated saponins from *Quillaja saponaria* may be conjugated to a lipid, fatty acid, polyethylene glycol, or terpene.

Alternatively, an active fragment or synthetically modified derivative of a fragment or a native saponin(s) may be utilized, such as those described in Soltysik et al., 1995, *Vaccine* 13(15):1403-1410; Marciani et al., 2000, *Vaccine* 18:3141-3151.Such modifications include but are not limited to removals or substitutions of saccharide residues, addition of saccharide residues, and removal, substitution and/or addition of acyl chains.

The methods and compositions of the present invention may also employ saponins isolated from plant species other than *Quillaja*, such as *Gypsophila* or *Saponaria officinalis* (Bomford et al., 1992, *Vaccine* 10(9):572-577,incorporated by reference herein in its entirety), and *Chenopodium quinoa* saponins (Estrada et al., 1998, *Comp. Immunol. Microbiol. Infect. Dis.* 21(3):225-36,incorporated by reference herein in its entirety).

In certain embodiments of the invention, compositions of the invention comprises saponins in combination with excipients. Preferably, the saponin is QS-21 and the excipients are selected from nonionic surfactants, polyvinyl pyrolidone, human serum albumin, and various unmodified and derivatized cyclodextrins. More preferably, in these embodiments, the nonionic surfactants are selected from Polysorbate 20,Polysorbate-40, Polysorbate-60,and Polysorbate-80.The polyvinyl pyrolidone may preferably be Plasdone C15,a pharmaceutical grade of polyvinyl pyrolidone. Preferred cyclodextrins are hydroxypropyl-β-cyclodextrin, hydroxypropyl-γ-cyclodextrin, and methyl-β-cyclodextrin. Preferably, the cyclodextrins are β-cyclodextrins. Examples of the excipients include those described in PCT/US98/17940,incorporated by reference herein in its entirety.

In another embodiment of the invention, compositions of the invention comprises saponins in combination with immunostimulatory polymers. Preferably, the saponin is QS-21 and the immunostimulatory polymers are selected from cytokines, muramyl dipeptides and tripeptide derivatives, CpG dinucleotides, CpG oligonucleotides, monophosphoryl Lipid A, and polyphosphazenes. Examples of the immunostimulatory polymers include those described in PCT/US00/23688.

There are multiple acceptable techniques for extraction and isolation of saponins from *Quillaja saponaria* Molina bark. Acceptable procedures for purifying the saponins of the present invention from *Quillaja saponaria* Molina bark, measuring the saponins for immune adjuvant activity, and characterizing the substantially pure saponins are disclosed in U.S. Pat. Nos. 5,057,540 and 5,583,112.

Aqueous extracts of *Quillaja saponaria* bark are also available commercially. These are dark brown, foamy extracts that contain many compounds (tannins, polyphenolics, saponins) that can be analyzed by a method such as reversed phase HPLC.

An example of a reversed phase HPLC analysis of a typical bark extract that is suitable for purification of saponins is shown in FIG. 1 of U.S. Pat. No. 6,231,859, which is incorporated herein in its entirety.

Partial purification to enrich the saponin fraction and to remove the majority of tannins and polyphenolics can be accomplished by dialysis of the extract against water through a 10,000 molecular weight membrane or ultrafiltration The saponin fraction is retained.

Alternatively, an aqueous saponin extract can be pretreated with polyvinylpolypyrrolidone to remove high molecular weight tannins and polyphenolics through absorption of these compounds.

Residual tannins and polyphenolics can then be removed from the saponin fraction by diafiltration against water. The saponin fraction, which forms micelles, is retained by ultrafiltration membranes of 10,000 to 30,000 molecular weight cutoff pore size. This yields a partially purified extract that consists predominantly of diverse saponins.

Separation of saponins can be accomplished by chromatography in organic solvents or organic solvent/water mixtures. A separation of saponins on silica was described in. U.S. Pat. No. 5,057,540.This yields saponins of intermediate purity (enriched in an individual saponin, but less than substantially pure).

Alternatively, other solvent systems on silica gel or the use of reverse phase chromatography can be used to accomplish the initial separation of saponins. This initial purification step can then typically be followed by reversed phase chromatography or similar HPLC step to purify the saponins to near homogeneity.

For example, saponin extract may be recovered from plant cell material freshly extracted from *Quillaja* trees. Dialyzed extract is then purified on an ion exchange column, e.g., the DE-52 type, followed by Sephadex G50 gel filtration. Ultrafiltration may be used instead of gel filtration. The purified saponin composition is then subjected to RP-HPLC analysis on a VYDAC C4 column, eluted with 30-45% acetonitrile in a 0.15% aqueous TFA-solution.

The substantially pure saponins useful in the present invention may also be isolated from fresh plant material consisting of substantially living cells as disclosed in WO 95/09179,or the previously described procedures.

The same procedure may be performed on plant cell material obtained by means of tissue culture or suspension cell culture. See, e.g., U.S. Pat. No. 5,716,848, which is incorporated herein by reference in its entirety.

General guidance on the use of saponins, Quil-A, and QS-21 can be found in the referenced patents. The amount of saponin present in a pharmaceutically effective composition should contain about 0.1 to 5,000 micrograms or more of a saponin. The amount of saponin present in a pharmaceutically effective composition is more preferably from about 1 to about 1000 micrograms, more preferably from about 5 to 500 micrograms, and most preferably from about 10 to 100 micrograms. In certain specific embodiments, the amount of saponin present in a pharmaceutical composition of the invention is 1, 2, 3, 5, 10, 15, 20, 25, 30, 40, 50, 60, 70, 80, 90, 100, 110, 125 or 150 micrograms.

Formulations of pharmaceutical compositions comprising saponins and procedures for their manufacture can be found in the literature and in the U.S. Patents incorporated by reference into this Description. Saponin formulations referred to are provided herein as nonlimiting examples.

In U.S. Pat. No. 5,583,112 at column 22,lines 11-17,a pharmaceutically effective composition for intradermal administration was made by reconstituting lyophilized "Quil A", a crude saponin mixture, into a phosphate buffered saline (PBS) solution and mixed with a solution containing 10 micrograms of Bovine Serum Albumin (BSA) to achieve a final volume of 200 microliters for intradermal injection. The effective amount of "Quil A" was found to be approximately 30-77 micrograms of "Quil A" by dry weight.

In U.S. Pat. No. 5,583,112 at column 23, lines 35-38, a pharmaceutically effective composition for subcutaneous administration was made by mixing a stock saline solution of ovalbumin and 10 micrograms of QS-21.

Also in U.S. Pat. No. 5,583,112 at Column 23, lines 35-38, a pharmaceutically effective composition for subcutaneous administration was made by chemically crosslinking QS-21 to lysozyme as described in Example 18 of the patent and resuspending lyophilized QS-21/lysozyme conjugate into 200 microliters of PBS (pH 7) for a final concentration of 10 micrograms of lysozyme and 1.6 micrograms of QS-21.

In a paper by Wu et al. (1994, *Cellular Immunology* 154:393-406), a pharmaceutically effective composition for subcutaneous or intraperitoneal administration is disclosed containing 25 micrograms ovalbumin absorbed to 250 micrograms of $Al(OH)_3$ and 20 micrograms of QS-21 per immunization dose.

In another paper by Wu et al. (1994, *J. Immun.* 148(5):1519-1525), a pharmaceutically effective composition for immunization is disclosed containing 25 micrograms of a truncated recombinant HIV-1 envelope protein absorbed to 250 micrograms of $Al(OH)_3$ and 10 micrograms of QS-21 in a sterile saline per immunization dose.

As a last non-limiting example, a pharmaceutically effective vaccine has recently been tested in human patients containing 5-500 micrograms of a synthetic nonapeptide and 100 micrograms of QS-21 in 500 microliters PBS (pH 7.4) per intradermally-administered dose (Lewis et al., 2000, *Int. J Cancer* 87(3):391-398).

The optimum amount of a specific saponin for use with a specific composition of the invention may vary. Optimization of the specific saponin amount for a given composition is, as demonstrated by the examples cited above, well within the purview of the skilled artisan.

4.3. Compositions of the Invention and Uses Thereof

The present invention encompasses therapies which involve administering an immunoreactive reagent and a saponin to an animal, preferably a mammal, and most preferably a human, for preventing, treating, or ameliorating symptoms associated with a disease, disorder, or infection. Prophylactic and therapeutic compounds of the invention include, but are not limited to, immunoreactive reagents and a saponin. Immunoreactive reagents such as antibodies may be provided in pharmaceutically acceptable compositions as known in the art or as described herein. The compositions of the invention can also be used in conjunction with other forms of therapy for a particular disease.

Compositions of the present invention can be administered to an animal, preferably a mammal and most preferably a human, to treat, prevent or ameliorate one or more symptoms associated with a disease, disorder, or infection. In a preferred embodiment, the composition of the invention exists outside of the body. Preferably, the immunoreactive reagent of the invention has been established to have some therapeutic benefit in the absence of saponin, and recognizes an epitope on a cell or molecule associated with the cause or symptoms of a disease, disorder or infection.

For example, the compositions and methods of the invention can also be used to prevent, inhibit or reduce the growth or metastasis of cancerous cells. In a specific embodiment, a composition comprising an immunoreactive reagent, such as an antibody, and saponin inhibits or reduces the growth or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth or metastasis in absence of said composition.

Each composition of the invention should contain at least one immunoreactive reagent (as defined herein, e.g., an antibody) and a saponin, and can then further comprise other reagents such as cytokines, growth factors, immunostimulatory oligonucleotides, and the like. One or more immunoreactive reagents that immunospecifically bind to one or more target antigens may be used locally or systemically in the body as a therapeutic. The immunoreactive reagents may also be advantageously utilized in combination with other such reagents such as monoclonal or chimeric antibodies, or with immune active compounds such as lymphokines or hematopoietic growth factors, such as, e.g., IL-2, IL-3 and IL-7 or immune response modifiers (IRMs, 3M Pharmaceuticals, St. Paul, Minn.), which, for example, serve to increase the number and/or activity of immune effector cells which act in conjunction with the immunoreactive reagent. In addition, immunostimulatory oligonucleotides may be used in combination with the saponin and immunoreactive reagents. Such oligonucleotides are known to enhance the immune response. Woolridge, et al., 1997, *Blood* 89:2994-2998. Such oligonucleotides are described in International Patent Publication Nos. WO 01/22972, WO 01/51083, WO 98/40100 and WO 99/61056, each of which is incorporated herein in its entirety, as well as U.S. Pat. Nos. 6,207,646 and 6,194,388, each of which is incorporated herein in its entirety. Such immunostimulatory oligonucleotides can comprise an unmethylated CpG motif. Other kinds of immunostimulatory oligos such as phosphorothioate oligodeoxynucleotides containing YpG- and CpR-motifs have been described by Kandimalla et al. in "Effect of Chemical Modifications of Cytosine and Guanine in a CpG-Motif of Oligonucleotides: Structure-Immunostimulatory Activity Relationships." *Bioorganic & Medicinal Chemistry* 9:807-813 (2001), incorporated herein by reference in its entirety. Methods of determining the activity of such oligonucleotides can be performed as described in the aforementioned patents and publications. Moreover, immunostimulatory oligonucleotides can be modified within the phosphate backbone, sugar, nucleobase and internucleotide linkages in order to modulate the activity. Such modifications are known to those of skill in the art.

The immunoreactive reagents and saponins of this invention may also be advantageously utilized in combination with one or more drugs used to treat a disease, disorder, or infection such as, for example anti-cancer agents, anti-inflammatory agents, or anti-bacterial/fungal or anti-viral agents. Examples of anti-cancer agents include, but are not limited to, cisplatin, ifosfamide, paclitaxel, taxanes, topoisomerase I inhibitors (e.g., CPT-11, topotecan, 9-ANTIGENIC COMPOSITION, and GG-211), gemcitabine, vinorelbine, oxaliplatin, 5-fluorouracil (5-FU), leucovorin, vinorelbine, temodal, and taxol.

In a specific embodiment, immunoreactive reagents administered to an animal are of a species origin or species reactivity that is the same species as that of the animal. Thus, in a preferred embodiment, human or humanized antibodies are administered to a human patient for therapy or prophylaxis.

The invention provides methods of treatment, prophylaxis, and amelioration of one or more symptoms associated with a disease, disorder or infection by administering to a subject of an effective amount of an immunoreactive reagent and a saponin, or pharmaceutical composition comprising an immunoreactive reagent and a saponin. In a preferred aspect, the immunoreactive reagent and saponin are substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as a cynomolgous monkey and a human). In a preferred embodiment, the subject is a human.

Various delivery systems are known and can be used to administer an immunoreactive reagent, e.g., encapsulation in liposomes, microparticles, microcapsules, recombinant cells capable of expressing the immunoreactive reagent, etc. Methods of administering an immunoreactive reagent and saponin or a pharmaceutical composition comprising the same include, but are not limited to, parenteral administration (e.g., intradermal, intramuscular, intraperitoneal, intravenous and subcutaneous), epidural, and mucosal (e.g., intranasal and oral routes). Preferably, the immunoreactive reagent is administered intravenously, while the saponin is not administered intravenously. In a specific embodiment, immunoreactive reagents, for example, antibodies, are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903,each of which is incorporated herein by reference in its entirety. In a preferred embodiment, an immunoreactive reagent is administered using Alkermes AIR™ pulmonary drug delivery technology (Alkermes, Inc., Cambridge, Mass.). Preferably, the saponin is not delivered by pulmonary administration.

In accordance with the present invention, a composition of the invention, comprising an immunoreactive reagent and a saponin is administered to a human subject with cancer, an infectious disease, or a neurodegenerative or amyloid diseases as a treatment. In one embodiment, "treatment" or "treating" refers to an amelioration of cancer, an infectious disease, or a neurodegenerative or amyloid disease, or at least one discernible symptom thereof. In another embodiment, "treatment" or "treating" refers to an amelioration of at least one measurable physical parameter associated with cancer, an infectious disease, a neurodegenerative or amyloid disease, not necessarily discernible by the subject. In yet another embodiment, "treatment" or "treating" refers to inhibiting the progression of a cancer, an infectious disease, a neurodegenerative or amyloid disease, either physically, e.g., stabilization of a discernible symptom, physiologically, e.g., stabilization of a physical parameter, or both. In yet another embodiment, "treatment" or "treating" refers to delaying the onset of a cancer, a neurodegenerative or amyloid disease.

In certain embodiments, the compositions of the present invention are administered to a human subject as a preventative measure against such cancer, an infectious disease, a neurodegenerative or amyloid disease. As used herein, "prevention" or "preventing" refers to a reduction of the risk of acquiring a given cancer, infectious disease, neurodegenerative or amyloid disease. In one mode of the embodiment, the compositions of the present invention are administered as a preventative measure to a human subject having a genetic predisposition to a cancer, infectious disease, neurodegenerative or amyloid disease. In another mode of the embodiment, the compositions of the present invention are administered as a preventative measure to a subject having a non-genetic predisposition to a cancer, or to a subject facing exposure to an agent of an infectious disease.

In a specific embodiment, it may be desirable to administer the pharmaceutical compositions of the invention locally to the area in need of treatment or prevention. In one embodiment, the treatment or prevention may be achieved by, for example, and not by way of limitation, local infusion, by injection, or by means of an implant, said implant being of a porous, non-porous, or gelatinous material, including membranes, such as sialastic membranes, or fibers. Preferably, care is taken to use materials to which the immunoreactive reagent does not absorb. In a particular embodiment, the immunoreactive reagent is administered systemically, for example, by i.v., and the saponin is administered locally to the area in need of treatment or prevention.

In another embodiment, the composition can be delivered in a vesicle, in particular a liposome (see Langer, *Science*, 249:1527-1533, 1990; Treat et al., in Liposomes in the Therapy of Infectious Disease and Cancer, Lopez-Berestein and Fidler (eds.), Liss, New York, pp. 353-365 (1989); Lopez-Berestein, ibid., pp. 3 17-327; see generally ibid.).

In yet another embodiment, the composition can be delivered in a controlled release or sustained release system. Any technique known to one of skill in the art can be used to produce sustained release formulations comprising one or more antibodies, or one or more fusion proteins. See, e.g., U.S. Pat. No. 4,526,938; PCT publication WO 91/05548; PCT publication WO 96/20698; Ning et al., "Intratumoral Radioimmunotheraphy of a Human Colon Cancer Xenograft Using a Sustained-Release Gel," *Radiotherapy & Oncology*, 39:179-189, 1996; Song et al., "Antibody Mediated Lung Targeting of Long-Circulating Emulsions," *PDA Journal of Pharmaceutical Science & Technology*, 50:372-397, 1995; Cleek et al., "Biodegradable Polymeric Carriers for a bFGF Antibody for Cardiovascular Application," *Pro. Intl. Symp. Control. Rel. Bioact. Mater.*, 24:853-854, 1997; and Lam et al., "Microencapsulation of Recombinant Humanized Monoclonal Antibody for Local Delivery," *Proc. Int'l. Symp. Control Rel. Bioact. Mater.*, 24:759-760, 1997,each of which is incorporated herein by reference in its entirety. In one embodiment, a pump may be used in a controlled release system (see Langer, supra; Sefton, 1987, *CRC Crit. Ref Biomed. Eng.* 14:20; Buchwald et al., 1980, *Surgery* 88:507; and Saudek et al., 1989, *N. Engl. J. Med.* 321:574). In another embodiment, polymeric materials can be used to achieve controlled release of immunoreactive reagents (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912, 015; 5,989,463; 5,128,326; PCT Publication No. WO 99/15154; and PCT Publication No. WO 99/20253). In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)).

Other controlled release systems are discussed in the review by Langer, 1990, *Science* 249:1527-1533).

The invention also provides that an immunoreactive reagent, for example an antibody, is packaged in a hermetically sealed container such as an ampoule or sachette indicating the quantity of immunoreactive reagent. In one embodiment, the immunoreactive reagent and saponin are supplied together or separately as dry sterilized lyophilized powders or water free concentrates in one or more hermetically sealed containers and can be reconstituted, e.g., with water or saline to the appropriate concentration for administration to a subject. The effective dosage of each immunoreactive reagent, and can be estimated initially from in vitro assays. It also depends on the nature of the target antigen, the density of the antigen in the tumors, the tumor type, the manner of administration, which can be optimized by a person skilled in the art without undue experimentation. Usual effective dosages for injection range from about 0.1 to 5 mg/kg/day, preferably from about 1 to 4 mg/kg/day, and more preferably from 2 to 4 mg/kg/week. Preferably, the immunoreactive reagent is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg.

In other embodiments, the saponin is QS-7, QS-17, QS-18, QS-21, QS-21-V1, or QS-21-V2. Preferably, the saponin is supplied at a unit dosage of at least 1 microgram, more preferably at least 10 micrograms, at least 15 micrograms, at least 25 micrograms, at least 35 micrograms, at least 45 micrograms, at least 50 micrograms, or at least 75 micrograms. In a preferred embodiment, the amount of saponin in the pharmaceutical composition is from about 0.1 to about 1000 micrograms. In a preferred embodiment, the amount of saponin is about 1, 2, 3, 5, 10, 15, 20, 25, 30, 40, 50, 60, 70, 80, 90, 100, 110, 125, 150, 200, 250, 300 or 500 micrograms. In a particularly preferred embodiment, the amount of saponin is 100 micrograms.

In a particularly preferred embodiment, the saponin is QS-21. The amount of QS-21 in the pharmaceutical compositions is preferably about 1 microgram or more. In a particularly preferred embodiment, the amount of QS-21 is from about 10 to about 1000 micrograms. In a particularly preferred embodiment, the amount of QS-21 is about 10 to 100 micrograms, or 20 to 50 micrograms, preferably 25 or 50 micrograms. The lyophilized immunoreactive reagent and saponin should be stored at between 2 and 8° C. in its original container and should be administered within 12 hours, preferably within 6 hours, within 5 hours, within 3 hours, or within 1 hour after being reconstituted. In an alternative embodiment, an immunoreactive reagent and saponin are supplied in liquid form in a hermetically sealed container indicating the quantity and concentration of the saponin and immunoreactive reagent. Preferably, the liquid form of the immunoreactive reagent is supplied in a hermetically sealed container at least 1 mg/ml, more preferably at least 2.5 mg/ml, at least 5 mg/ml, at least 8 mg/ml, at least 10 mg/ml, at least 15 mg/ml, or at least 25 mg/ml. Preferably, the liquid form of the saponin is supplied in a hermetically sealed container at least 1 mg/ml, more preferably at least 2.5 mg/ml, at least 5 mg/ml, at least 8 mg/ml, at least 10 mg/ml, at least 15 mg/ml, or at least 25 mg/ml.

The present invention also provides pharmaceutical compositions. Such compositions comprise a prophylactically or therapeutically effective amount of an immunoreactive reagent and a saponin, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., MPL, immunostimulatory oligonucleotides, Freund's complete and incomplete, mineral gels such as aluminum hydroxide, surface active substances such as lysolecithin, pluronic polyols, polyanions, peptides, oil emulsions, keyhole limpet hemocyanins, dinitrophenol, and potentially useful adjuvants for humans such as BCG (Bacille Calmette-Guerin) and *Corynebacterium parvum*), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents: These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a prophylactically or therapeutically effective amount of the immunoreactive reagent and saponin, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Preferably, the saponin is not administered intravenously.

Generally, the ingredients of compositions of the invention are supplied as a kit either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In another embodiment, a kit of the invention further comprises a needle or syringe, preferably packaged in sterile form, for injecting the composition, and/or a packaged alcohol pad. Instructions are optionally included for administration of the compositions of the invention by a clinician or by the patient.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment; prevention or amelioration of one or more symptoms associated with a disease, disorder, or infection can be determined by standard clinical techniques. The precise dose to be employed in the formulation will depend on the route of administration, the age of the subject, and the seriousness of the disease, disorder, or infection, and should be decided according to the judgment of the practitioner and each patient's circumstances. Effective doses may be extrapolated from dose-response curves derived from in vitro or animal model (e.g., the cotton rat or Cynomolgous monkey) test systems. Models and methods for evaluation of the effects of saponins and antibodies, or other immunoreactive reagents are known in the art. (Wooldridge et al., *Blood*, 1997, 89 (8): 2994-2998, incorporated by reference herein in its entirety).

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage will, however, depend upon the extent to which the serum half-life of the molecule has been increased. Generally, human antibodies have longer half-lives within the human body than antibodies from other species due to the immune response to the foreign polypeptides. Thus, lower dosages of human antibodies and less frequent administration is often possible. Further, the dosage and frequency of administration of immunoreactive reagents may be reduced also by enhancing uptake and tissue penetration (e.g., into the lung) of the immunoreactive reagents such as, for example, lipidation.

Treatment of a subject with a therapeutically or prophylactically effective amount of an immunoreactive reagent and saponin can include a single treatment or, preferably, can include a series of treatments. In a preferred example, a subject is treated with an immunoreactive reagent in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In a preferred example, a subject is treated with a saponin in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical composition of the invention is administered once a day, twice a day, or three times a day. In other embodiments, the pharmaceutical composition is administered once a week, twice a week, once every two weeks, once a month, once every six weeks, once every two months, twice a year or once per year. It will also be appreciated that the effective dosage of the immunoreactive reagents used for treatment may increase or decrease over the course of a particular treatment. The immunoreactive reagent and the saponin can be administered simultaneously. In a preferred embodiment, the saponin and immunoreactive reagent are administered at different times. In one embodiment, the immunoreactive reagent is administered prior to the saponin, e.g., at least 7 days, 3 days, 2 days, 1 day, 16 hours, 12 hours, 8 hours, 4 hours, 2 hours or 1 hour prior. In a preferred embodiment, the saponin is administered prior to the immunoreactive reagent, e.g., at least 7 days, 3 days, 2 days, 1 day, 16 hours, 12 hours, 8 hours, 4 hours, 2 hours or 1 hour prior.

4.4. Methods of Making Pharmaceutical Compositions Comprising an Immunoreactive Reagent and a Saponin The present invention encompasses methods of making pharmaceutical compositions comprising a saponin and an immunoreactive reagent.

In one embodiment, the saponin is combined with the immunoreactive reagent. In a preferred embodiment, the saponin and immunoreactive reagent are formulated separately, and are in separate containers within a kit. Such a kit can optionally further comprise instructions for the administration of the immunoreactive reagent and saponin.

5. EXAMPLES 5.1. Enhancement of Antibody Mediated Lysis in vitro

Murine splenocytes (effector cells) are generated from the spleens of naive 6-8week old mice. These effector cells are incubated with 1 to 10 ug/ml of QS-21 or appropriate amount of another immunomodulatory saponin for 24 to 72 hours. At the end of the incubation period, target cells (E.G7-OVA or MO4) are loaded with 51 Cr. Effector cells and labeled target cells are incubated at defined effector:target ratios in the presence and absence of monoclonal antibody to SIINFEKL (SEQ ID NO: 1)/Class I MHC (1 to 10 ug/ml) at 4° C. for 30 to 60minutes. The lysis in the presence of QS-21 and monoclonal is compared to controls without QS-21, without monoclonal, or both. There is an enhanced lysis due to QS-21 (determined by the fold-enhancement of lysis due to QS-21 /monoclonal over monoclonal alone).

5.2. Improvement of Protection in Tumor Challenge Model

C57B1/6 mice are inoculated by s.c. route in the flank with MO4 tumor ($1 \times 10^5$) or EG7-OVA tumor. At 24 to 48 hours after inoculation, mice are injected by IP route with a monoclonal antibody to SIINFEKL (SEQ ID NO: 1)/Class I MHC , or by local SC route in the presence or absence of QS-21 (10 -20 ug). The antitumor effect of the QS-21/monoclonal antibody treatment is compared to that of monoclonal antibody treatment by monitoring the growth of the tumors over a 30 to 60 day period (measurement with calipers). Survival was determined, and significance with respect to time to death was assessed using Cox regression analysis. Mice were also observed daily for signs of toxicity including level of activity, ruffled fur, diarrhea, and general appearance. A significant number of mice treated with monoclonal antibody alone developed tumor compared with those treated with antibody and QS-21. The benefit of the QS-21 treatment is demonstrated by a delay in tumor progression. Models and methods for evaluation of the effects of saponins and antibodies, or other immunoreactive reagents are known in the art. (Wooldridge et al., *Blood,* 1997, 89 (8): 2994-2998, incorporated by reference herein in its entirety).

5.3. Improved Opsonization of Bacteria by Use of QS-21

Improved opsonization of bacteria by saponin is demonstrated in vitro by incubating effector cells for the opsonophagocytosis assay (HL-60) with QS-21. The cells are evaluated for whether they are more effective in opsonizing *S. pneumonia* or *S. aureus* at a given antibody titer (for example a human serum sample with opsonizing activity specific for *S. pneumonia* or *S. aureus*, respectively).

5.4. The Upregulation by QS-21 of Fc Receptors

Monocytes, natural killer cells, or polymorphonuclear cells are incubated in the presence or absence of QS-21 (for example 1-10 ug/ml). The trypsinized cells are incubated at 4° C. for 60 min with monoclonal antibodies specific to Fc α R, Fc gamma R1, Fc gamma RII or Fc gamma RIII. The cells are then incubated with an anti-mouse IgG FITC probe, washed, fixed in paraformaldehyde, and analyzed by FACScan. Upregulation of Fc receptors on these cells is demonstrated.

In addition, upregulation of TNF-alpha, IL-6 and MIP-1-alpha by QS-21 in macrophage cells was demonstrated. In bone marrow derived dendritic cells, QS-21 was found to increase production of MIP-1-alpha and IL-1, and to decrease the production of II-12 and MIP-1-beta.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of each of which are incorporated by reference herein in their entireties.

What is claimed is:

1. A method of treating cancer in an individual in whom such treatment is desired, comprising administering to the individual:
   (i) an immunoreactive reagent that specifically binds to a tumor-associated antigen of said type of cancer, and
   (ii) a saponin,
   wherein said immunoreactive reagent and said saponin are administered by different routes of administration and wherein said saponin is not administered intravenously, and wherein said saponin enhances the anti-tumor efficacy of said immunoreactive reagent.

2. A method of treating an infectious disease in an individual in whom such treatment is desired, comprising administering to the individual:
   (i) an immunoreactive reagent that specifically binds to an antigen of an agent of said infectious disease, and
   (ii) a saponin,
   wherein said immunoreactive reagent and said saponin are administered by different routes of administration and wherein said saponin is not administered intravenously, and wherein said saponin enhances the efficacy of said immunoreactive reagent.

3. The method of claim 1, wherein the immunoreactive reagent is an antibody.

4. The method of claim 1, wherein the amount of saponin is at least 1 microgram.

5. The method of claim 4, wherein the amount of saponin is 10 to 20 micrograms.

6. The method of claim 5, wherein the amount of saponin is 20 to 100 micrograms.

7. The method of claim 5, wherein the amount of saponin is 100 to 500 micrograms.

8. The method of claim 1, wherein the saponin is QS-7, QS-17, QS-18, QS-21, QS-21-V1, or QS-21-V2.

9. The method of claim 8, wherein the saponin is QS-21.

10. The method of claim 1, wherein the saponin is administered prior to the immunoreactive reagent.

11. The method of claim 10, wherein the saponin is administered at least one day prior to the immunoreactive reagent.

12. The method of claim 1, wherein said immunoreactive reagent is administered by systemic administration.

13. The method of claim 12, wherein said immunoreactive reagent is administered by intravenous administration.

14. The method of claim 13, wherein said saponin is administered by a route selected from the group consisting of intradermal, subcutaneous and intraperitoneal.

15. A method of enhancing antibody dependent cellular cytotoxicity or phagocytosis of a target in an individual in whom such enhancement is desired, comprising administering to the individual:
   (i) an immunoreactive reagent that specifically binds to an antigen of said target, and
   (ii) a saponin,
   wherein said immunoreactive reagent and said saponin are administered by different routes of administration and wherein said saponin is not administered intravenously, and wherein said saponin enhances the efficacy of said immunoreactive reagent.

16. A method of enhancing passive immunotherapy in an individual in whom such enhancement is desired, wherein said immunotherapy comprises administering to the individual:
   (i) an immunoreactive reagent that specifically binds to an antigen of a target, and
   (ii) a saponin,
   wherein said immunoreactive reagent and said saponin are administered by different routes of administration and wherein said saponin is not administered intravenously, and wherein said saponin enhances the efficacy of said immunoreactive reagent.

17. The method of claim 1, wherein said immunoreactive reagent and said saponin are administered at different times from one another.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Ile Ile Asn Phe Glu Lys Leu
1               5
```